(12) United States Patent
Rioux

(10) Patent No.: US 7,527,633 B2
(45) Date of Patent: May 5, 2009

(54) METHODS AND DEVICES FOR THE TREATMENT OF URINARY INCONTINENCE

(75) Inventor: Robert F. Rioux, Ashland, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 806 days.

(21) Appl. No.: 09/874,302

(22) Filed: Jun. 5, 2001

(65) Prior Publication Data

US 2001/0053916 A1    Dec. 20, 2001

Related U.S. Application Data

(60) Provisional application No. 60/209,234, filed on Jun. 5, 2000.

(51) Int. Cl.
*A61B 17/04* (2006.01)

(52) U.S. Cl. .................. 606/148; 606/144; 606/150

(58) Field of Classification Search .......... 606/148, 606/144, 150, 139, 138, 190, 145–147, 228, 606/233; 128/340; 604/143
See application file for complete search history.

(56) References Cited

U.S. PATENT DOCUMENTS

| | | | |
|---|---|---|---|
| 2,751,903 A | 6/1956 | Ivory et al. ................... 128/20 |
| 2,917,878 A | 12/1959 | Edwin et al. | |
| 3,372,477 A * | 3/1968 | Hoppe .......................... 606/138 |
| 3,472,232 A | 10/1969 | Earl et al. | |
| 3,565,073 A | 2/1971 | Giesy | |
| 3,699,969 A | 10/1972 | Allen ........................... 128/330 |
| 3,704,712 A | 12/1972 | Giesy et al. | |
| 3,710,795 A | 1/1973 | Higuchi et al. | |
| 3,763,860 A | 10/1973 | Clarke | |
| 3,875,937 A | 4/1975 | Schmitt et al. | |
| 3,877,434 A | 4/1975 | Ferguson et al. ............ 128/327 |
| 3,937,223 A | 2/1976 | Roth | |
| 3,995,619 A | 12/1976 | Glatzer ........................ 128/2 B |
| 4,172,458 A | 10/1979 | Pereyra ....................... 128/340 |
| 4,363,319 A | 12/1982 | Altschuler | |

(Continued)

FOREIGN PATENT DOCUMENTS

DE    2305815 A1    8/1974

(Continued)

OTHER PUBLICATIONS

"A Modified Percutaneous Outpatient Bladder Neck Suspension System" by Theodore V. Benderev, Dec. 1994, The Journal of Urology.*

(Continued)

*Primary Examiner*—Steven O Douglas
(74) *Attorney, Agent, or Firm*—Ropes & Gray LLP

(57) ABSTRACT

Methods and devices for treating female stress urinary incontinence are disclosed. The methods include transvaginally accessing the pelvic cavity and introducing a suburethral sling into the retropubic space. In some embodiments the ends of the sling are attached to an anatomical support structure. In other embodiments, the ends of the suburethral sling are not attached to an anatomical support structure. The devices include a surgical instrument for blunt dissection of the pelvic cavity which includes a curved shaft and a blunt distal end. A hook deployment device may optionally be attached to the surgical instrument.

17 Claims, 5 Drawing Sheets

U.S. PATENT DOCUMENTS

| | | | |
|---|---|---|---|
| 4,367,816 A | 1/1983 | Wilkes | |
| 4,422,567 A | 12/1983 | Haynes | 227/19 |
| 4,445,898 A | 5/1984 | Jensen | |
| 4,535,768 A | 8/1985 | Hourahane et al. | 128/305.1 |
| 4,583,540 A | 4/1986 | Malmin | |
| 4,606,335 A | 8/1986 | Wedeen | 128/92 E |
| 4,739,751 A | 4/1988 | Sapega et al. | 128/92 V |
| 4,741,330 A | 5/1988 | Hayhurst | 128/92 YF |
| 4,744,353 A | 5/1988 | McFarland | 128/92 VD |
| 4,776,337 A | 10/1988 | Palmaz | |
| 4,784,137 A | 11/1988 | Kulik et al. | 128/334 R |
| 4,784,138 A | 11/1988 | Sinnett | 128/334 R |
| 4,798,193 A | 1/1989 | Giesy et al. | |
| 4,824,435 A | 4/1989 | Giesy et al. | |
| 4,872,451 A | 10/1989 | Moore et al. | |
| 4,873,977 A | 10/1989 | Avant et al. | 128/334 R |
| 4,874,375 A | 10/1989 | Ellison | 604/164 |
| 4,896,668 A | 1/1990 | Popoff et al. | |
| 4,920,958 A | 5/1990 | Walt et al. | 606/96 |
| 4,927,420 A | 5/1990 | Newkirk et al. | 606/45 |
| 4,938,760 A | 7/1990 | Burton et al. | 600/29 |
| 4,946,468 A | 8/1990 | Li | |
| 4,983,168 A | 1/1991 | Moorehead | |
| 4,988,339 A | 1/1991 | Vadher | |
| 5,002,550 A | 3/1991 | Li | |
| 5,013,292 A | 5/1991 | Lemay | 600/30 |
| 5,064,435 A | 11/1991 | Porter | |
| 5,078,730 A | 1/1992 | Li | |
| 5,084,058 A | 1/1992 | Li | |
| 5,085,661 A | 2/1992 | Moss | 606/139 |
| 5,087,263 A | 2/1992 | Li | 606/148 |
| 5,089,013 A | 2/1992 | Bezwada et al. | 606/228 |
| 5,112,344 A | 5/1992 | Petros | 606/148 |
| 5,133,723 A | 7/1992 | Li et al. | 606/148 |
| 5,149,329 A | 9/1992 | Richardson | 604/272 |
| 5,152,749 A | 10/1992 | Giesy et al. | |
| 5,163,946 A | 11/1992 | Li | 606/148 |
| 5,167,634 A | 12/1992 | Corrigan et al. | |
| 5,188,636 A | 2/1993 | Fedotov | 606/144 |
| 5,203,784 A | 4/1993 | Ross et al. | 606/104 |
| 5,207,679 A | 5/1993 | Li | |
| 5,222,508 A | 6/1993 | Contarini | 128/898 |
| 5,234,457 A | 8/1993 | Anderson | |
| 5,250,033 A | 10/1993 | Evans | |
| 5,256,133 A | 10/1993 | Spitz | 600/29 |
| 5,279,311 A | 1/1994 | Snyder | 128/898 |
| 5,281,237 A | 1/1994 | Gimpolson | 606/144 |
| 5,282,812 A | 2/1994 | Suarez, Jr. | |
| 5,324,306 A | 6/1994 | Markower et al. | |
| 5,334,185 A | 8/1994 | Giesy et al. | |
| 5,337,736 A | 8/1994 | Reddy | 128/20 |
| 5,368,595 A | 11/1994 | Lewis | |
| 5,379,496 A | 1/1995 | Krauss | |
| 5,409,469 A | 4/1995 | Schaerf | |
| 5,417,226 A | 5/1995 | Juma | |
| 5,431,173 A | 7/1995 | Chin et al. | 128/898 |
| 5,437,682 A * | 8/1995 | Grice et al. | 606/148 |
| 5,439,467 A * | 8/1995 | Benderev et al. | 606/139 |
| 5,441,502 A | 8/1995 | Bartlett | 606/104 |
| 5,474,543 A | 12/1995 | McKay | 604/272 |
| 5,499,991 A | 3/1996 | Garman et al. | 606/148 |
| 5,505,735 A | 4/1996 | Li | |
| 5,536,273 A * | 7/1996 | Lehrer | 606/139 |
| 5,544,664 A | 8/1996 | Benderev et al. | 128/898 |
| 5,562,717 A | 10/1996 | Tippey et al. | |
| 5,582,188 A | 12/1996 | Benderev et al. | |
| 5,591,163 A | 1/1997 | Thompson | |
| 5,611,515 A | 3/1997 | Benderev et al. | |
| 5,620,012 A | 4/1997 | Benderev et al. | |
| 5,624,446 A | 4/1997 | Harryman, II | |
| 5,626,614 A | 5/1997 | Hart | |
| 5,637,112 A | 6/1997 | Moore et al. | |
| 5,643,288 A | 7/1997 | Thompson | |
| 5,645,589 A | 7/1997 | Li | |
| 5,647,857 A | 7/1997 | Anderson et al. | |
| 5,683,418 A | 11/1997 | Luscombe et al. | |
| 5,690,649 A | 11/1997 | Li | |
| 5,697,931 A | 12/1997 | Thompson | |
| 5,700,266 A | 12/1997 | Harryman, II | |
| 5,700,286 A | 12/1997 | Tartaglia et al. | |
| 5,702,215 A | 12/1997 | Li | |
| 5,742,943 A | 4/1998 | Chen | |
| 5,749,884 A | 5/1998 | Benderev et al. | |
| 5,766,221 A | 6/1998 | Benderev et al. | |
| 5,776,184 A | 7/1998 | Tuch | |
| 5,813,408 A | 9/1998 | Benderev et al. | |
| 5,814,072 A | 9/1998 | Bonutti | |
| 5,816,258 A | 10/1998 | Jervis | |
| 5,824,049 A | 10/1998 | Ragheb et al. | |
| 5,836,314 A * | 11/1998 | Benderev et al. | 128/898 |
| 5,836,315 A | 11/1998 | Benderev et al. | |
| 5,840,011 A | 11/1998 | Landgrebe et al. | |
| 5,842,478 A | 12/1998 | Benderev et al. | |
| 5,860,993 A | 1/1999 | Thompson et al. | |
| 5,899,909 A | 5/1999 | Claren et al. | 606/119 |
| 5,904,692 A | 5/1999 | Steckel et al. | |
| 5,935,122 A | 8/1999 | Fourkas et al. | |
| 5,954,057 A | 9/1999 | Li | |
| 5,997,541 A | 12/1999 | Schenk | |
| 6,001,104 A | 12/1999 | Benderev et al. | |
| 6,039,686 A | 3/2000 | Kovac | |
| 6,042,534 A | 3/2000 | Gellman et al. | |
| 6,042,583 A | 3/2000 | Thompson et al. | |
| 6,050,937 A | 4/2000 | Benderev | |
| 6,056,688 A | 5/2000 | Benderev et al. | |
| 6,059,801 A | 5/2000 | Samimi | |
| 6,077,216 A | 6/2000 | Benderev et al. | |
| 6,096,041 A | 8/2000 | Gellman et al. | |
| 6,099,538 A | 8/2000 | Moses et al. | 606/144 |
| 6,099,547 A | 8/2000 | Gellman et al. | |
| 6,117,067 A | 9/2000 | Gil-Vernet | |
| 6,200,330 B1 | 3/2001 | Benderev et al. | |
| 6,245,082 B1 | 6/2001 | Gellman et al. | |
| 6,254,620 B1 * | 7/2001 | Koh et al. | 606/167 |
| 6,264,676 B1 | 7/2001 | Gellman et al. | |
| 6,273,852 B1 | 8/2001 | Lehe et al. | |
| 6,299,607 B1 | 10/2001 | Osborn, III et al. | |
| 6,312,448 B1 | 11/2001 | Bonutti | |
| 6,322,492 B1 | 11/2001 | Kovac | |
| 6,328,686 B1 | 12/2001 | Kovac | |
| 6,382,214 B1 | 5/2002 | Raz et al. | |
| 6,406,423 B1 | 6/2002 | Scetbon | |
| 6,423,080 B1 | 7/2002 | Gellman et al. | |
| 6,440,154 B2 | 8/2002 | Gellman et al. | |
| D466,213 S | 11/2002 | Snitkin et al. | |
| 6,478,727 B2 | 11/2002 | Scetbon | |
| 6,478,763 B1 | 11/2002 | Simonsen et al. | |
| 6,491,703 B1 | 12/2002 | Ulmsten | |
| 6,494,887 B1 | 12/2002 | Kaladelfos | |
| 6,500,194 B2 | 12/2002 | Benderev et al. | |
| 6,502,578 B2 | 1/2003 | Raz et al. | |
| 6,530,943 B1 | 3/2003 | Hoepffner et al. | |
| 6,605,097 B1 | 8/2003 | Lehe et al. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,638,211 B2 | 10/2003 | Suslian et al. | |
| 6,641,525 B2 | 11/2003 | Rocheleau et al. | |
| 6,648,921 B2 | 11/2003 | Anderson et al. | |
| 6,652,450 B2 | 11/2003 | Neisz et al. | |
| 6,685,629 B2 | 2/2004 | Therin | |
| 6,691,711 B2 | 2/2004 | Raz et al. | |
| 6,723,107 B1 | 4/2004 | Skiba et al. | |
| 6,911,003 B2 | 6/2005 | Anderson et al. | |

| | | | |
|---|---|---|---|
| 6,936,054 B2 * | 8/2005 | Chu | 606/145 |
| 6,960,160 B2 | 11/2005 | Browning | |
| 6,991,635 B2 * | 1/2006 | Takamoto et al. | 606/144 |
| 7,160,314 B2 | 1/2007 | Sgro et al. | |
| 2001/0000533 A1 | 4/2001 | Kovac | |
| 2001/0018549 A1 | 8/2001 | Scetbon | |
| 2001/0023356 A1 | 9/2001 | Raz et al. | |
| 2001/0049467 A1 | 12/2001 | Lehe et al. | |
| 2001/0053916 A1 | 12/2001 | Rioux | |
| 2002/0013590 A1 | 1/2002 | Therin et al. | |
| 2002/0022841 A1 | 2/2002 | Kovac | |
| 2002/0055748 A1 | 5/2002 | Gellman et al. | |
| 2002/0068948 A1 | 6/2002 | Stormby et al. | |
| 2002/0072694 A1 | 6/2002 | Snitkin | |
| 2002/0077526 A1 | 6/2002 | Kammerer et al. | |
| 2002/0082619 A1 | 6/2002 | Cabak et al. | |
| 2002/0091298 A1 | 7/2002 | Landgrebe | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslian et al. | |
| 2002/0107430 A1 | 8/2002 | Neisz et al. | |
| 2002/0116025 A1 | 8/2002 | Haab | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151910 A1 | 10/2002 | Gellman et al. | |
| 2002/0161382 A1 | 10/2002 | Neisz et al. | |
| 2002/0165566 A1 | 11/2002 | Ulmsten | |
| 2002/0188169 A1 | 12/2002 | Kammerer et al. | |
| 2003/0004395 A1 | 1/2003 | Therin | |
| 2003/0004580 A1 | 1/2003 | Sump et al. | |
| 2003/0010929 A1 | 1/2003 | Priewe et al. | |
| 2003/0018350 A1 * | 1/2003 | Zucherman et al. | 606/190 |
| 2003/0023138 A1 | 1/2003 | Luscombe | |
| 2003/0036676 A1 | 2/2003 | Scetbon | |
| 2003/0045774 A1 | 3/2003 | Staskin et al. | |
| 2003/0045892 A1 | 3/2003 | Kaladelfos | |
| 2003/0050530 A1 | 3/2003 | Neisz et al. | |
| 2003/0100954 A1 | 5/2003 | Schuldt-Hempe et al. | |
| 2003/0130670 A1 | 7/2003 | Anderson et al. | |
| 2003/0176762 A1 | 9/2003 | Kammerer | |
| 2003/0181926 A1 * | 9/2003 | Dana et al. | 606/148 |
| 2003/0191480 A1 | 10/2003 | Ulmsten et al. | |
| 2004/0015048 A1 | 1/2004 | Neisz et al. | |
| 2004/0176802 A1 * | 9/2004 | Skiba et al. | 606/222 |
| 2005/0021055 A1 * | 1/2005 | Toubia et al. | 606/144 |
| 2005/0131393 A1 * | 6/2005 | Chu et al. | 606/1 |
| 2005/0203562 A1 * | 9/2005 | Palmer et al. | 606/190 |
| 2005/0222601 A1 * | 10/2005 | Erhard | 606/190 |

FOREIGN PATENT DOCUMENTS

| | | | |
|---|---|---|---|
| DE | 2532242 A1 | 2/1977 | |
| DE | 43 34 419 A1 | 4/1995 | |
| DE | 200 16 866 U 1 | 12/2000 | |
| EP | 0 140 557 A3 | 5/1985 | |
| EP | 0437063 A2 | 7/1991 | |
| EP | 0437063 A3 | 7/1991 | |
| EP | 0 599 772 A1 | 6/1994 | |
| EP | 0668056 | 8/1995 | |
| EP | 0 506 920 B1 | 4/1997 | |
| EP | 0 417 189 B1 | 10/1997 | |
| EP | 0 628 288 B1 | 4/2000 | |
| EP | 1 159 920 A2 | 12/2001 | |
| EP | 1 201 189 | 5/2002 | |
| EP | 0 831 751 B1 | 11/2002 | |
| EP | 1 321 111 | 6/2003 | |
| EP | 1342450 | 9/2003 | |
| FR | 1539593 | 9/1968 | |
| FR | 2739016 | 3/1997 | |
| GB | 2268690 | 1/1994 | |
| PL | 0437063 A2 * | 12/1990 | |
| SE | 503 271 | 3/1996 | |
| SE | 506 164 | 4/1997 | |
| SU | 1225547 | 4/1986 | |
| SU | 1443873 | 12/1988 | |
| SU | 1443873 A1 | 7/1989 | |
| WO | 93/10715 | 6/1993 | |
| WO | 93/19678 | 10/1993 | |
| WO | WO-96/01597 | 1/1996 | |
| WO | WO-96/34587 | 11/1996 | |
| WO | WO-96/39227 | 12/1996 | |
| WO | 97/13465 | 4/1997 | |
| WO | 98/12971 | 4/1998 | |
| WO | WO-98/19606 | 5/1998 | |
| WO | WO-98/34545 | 8/1998 | |
| WO | WO-99/59477 | 11/1999 | |
| WO | WO-00/74594 | 12/2000 | |
| WO | WO-01/78609 | 10/2001 | |
| WO | WO-01/53916 | 12/2001 | |
| WO | WO-02/058564 | 8/2002 | |

OTHER PUBLICATIONS

Bayer et al. A New Approach to Primary Strengthening of Colostomy with Marlex Mesh to Prevent Paracolostomy Hernia. Surgery, Gynecology & Obstretrics. 163:579-80 (1986).

Delorme, E. La bandelette trans-obturatrice: un procede mini-invasif pour traiter l'incontinence urinaire d'effort de la femme. Progres en Urologie. 11:1306-13 (2001) (English translation provided).

Giesy et al. Ureteral Instrumentation: A New System for Continued Access Via a Safety Guidewire. Journal of Urology. No. 4, Part 2, p. 282A (1988).

Gittes et al. No-Incision Pubovaginal Suspension for Stress Incontinence. Journal of Urology. 138:3, 568-70 (1987).

Haab et al. Feasibility of Outpatient Percutaneous Bladder Neck Suspension Under Local Anesthesia. Urology. 50:4, 585-897 (1997).

Jacquetin, B. Utilisation du TVT dans la chirurgie de l'incontinence urinaire feminine. J. Gynecol Obstet Biol Reprod. 29, 242-47 (2000).

Kovac et al. Pubic Bone Suburethral Stabilization Sling for Recurrent Urinary Incontinence. Obstetrics & Gynecology, 89:4, 624-27 (1997).

Norris et al. Use of Synthetic Material in Sling Surgery: A Minimally Invasive Approach. Journal of Endourology. 10:3, 227-30 (1996).

Petros et al. An Integral Theory and Its Method for the Diagnosis and Management of Female Urinary Incontinenece. Scandinavian Journal of Urology and Nephrology. Supplement 153, 1-93 (1993).

Petros et al. Urethral Pressure Increase on Effort Originates from Within the Urethra, and Continence From Musculovaginal Closure. Neurourology and Urodynamics. 14:4, 337-50 (1995).

Petros, P. Ambulatory surgery for urinary incontinence and vaginal prolapse. Medical Journal of Australia. 161:171-72 (1994).

Petros, P. Medium-term Follow-up of the Intravaginal Slingplasty Operation Indicates Minimal Deterioration of Urinary Continence with Time. Aust NZ J Obstet Gynaecol. 39:3, 354-56 (1999).

Petros, P. The Intravaginal Slingpasty Operation, a Minimally Invasive Technique for Cure of Urinary Incontinence in the Female. Aust. NZ J Obstet Gynaecol. 36:4, 453-61 (1996).

Petros, P. An Integral Theory of Bladder Neck Opening, Closure and Urinary Incontinence in the Female. International Journal of Gynecology & Obstetrics. XXIII World Congress of Gynaecology and Obstetrics (FIGO) 1991.

Raz et al. Vaginal Wall Sling. The Journal of Urology. 141:43-6 (1989).

Raz et al. Fascial Sling to Correct Male Neurogenic Sphincter Incompetence: The McGuire/Raz Approach. Journal of Urology. 139:528-31 (1988).

Raz, S. Modified Bladder Neck Suspension for Female Stress Incontinence. Urology. 17:1, 82-5 (1981).

Stamey, T.A. Endoscopic Suspension of the Vesical Neck for Urinary Incontinence in Females. Annals of Surgery. 192:4, 465-71 (1980).

Stamey, T.A. Endoscopic Suspension of the Vesical Neck for Urinary Incontinence. Surgery, Gynecology & Obstetrics. 136:4, 547-54 (1973).

Stamey, T.A. Endoscopic Suspension of the Vesical Neck. Stanton, Tanagho (eds.). Surgery of Female Incontinence. Springer-Verlag, Berlin; 115-32 (1986).

Staskin et al. The Gore-tex sling procedure for female sphincteric Incontinence: Indications, technique, and results. World J of Urol. 15:5, 295-99 (1997).

Staskin, D.R. Sling Surgery for the Treatment of Female Stress Incontinence. 5:1, 106-22 (1991).

Sussman, et al. The Raz Bladder Neck Suspension: Five-Year Experience. The Journal of Urology. 145, 223A (1993).

Ulmsten et al. A Multicenter Study of Tension-Free Vaginal Tape (TVT) for Surgical Treatment of Stress Urinary Incontinence. Int Urogynecol J. 9:4, 210-13 (1998).

Ulmsten et al. A Three-Year Follow Up of Tension Fee Vaginal Tape for Surgical Treatment of Female Stress Urinary Incontinence. British Journal of Obstetrics and Gynaecology. 106, 345-50 (1999).

Ulmsten et al. An Ambulatory Surgical Procedure Under Local Anesthesia for Treatment of Female Urinary Incontinence. The International Urogynecology Journal. 7:81-86 (1996).

Ulmsten et al. Connective Tissue Factors in the Aetiology of Femal Pelvic Disorders. Ann. Med. 22:6, 3 (1990).

Ulmsten et al. Intravaginal Slingplasty (IVS): An Ambulatory Surgical Procedure for Treatment of Female Urinary Incontinence. Scand J Urol Nephrol 29:1, 75-82 (1995).

Ulmsten et al. Surgery for female urinary incontinence. Current Opinion in Obstetrics & Gynecology. 4:3, 456-62 (1992).

Ulmsten et al. Intravaginal slingplasty. Zentralbl Gynakol. 116, 398-404 (1994).

Ulmsten, U. An Introduction to Tension-Free Vaginal Tape (TVT)—A New Surgical Procedure for Treatment of Female Urinary Incontinence. Int Urogynecol J. (Suppl 2): S3-4 (2001).

Ulmsten, U. The basic understanding and clinical results of tension-free vaginal tape for stress urinary incontinence. Der Urologe [A] 40:269-73 (2001).

European Search Report dated Sep. 29, 2006 from corresponding Application No. EP 05 02 5122.

Benderev: Anchor Fixation And Other Modifications Of Endoscopic Bladder Neck Suspension, Urology 40: 409-418 (1992).

Benderev: A New Endoscopic Bladder Neck Suspension for the Outpatient Treatment of Stress Urinary Incontinence, (video v-40) J. Urology 149: 197A (1993).

Benderev: A Modified Percutaneous Outpatient Bladder Neck Suspension System, J. Urology 152: 2316-2320 (1994).

Leach et al,: Modified Pereyra Bladder Neck Suspension After Previously Failed Anti-Incontinence Surgery: Surgical Technique and Results with Long-Term Follow-Up, Urology 23: 359-362 (1984).

Mattox et al.: Modification of the Miya Hook in Vaginal Colpopexy, The Journal of Reproductive Medicine, 40: 681-683 (Oct. 1995).

Mitchell: Hook Needle and Retractor for Posterior Urethroplasty, J. Urology 42: 599-600 (1970).

Nativ et al.: Bladder Neck Suspension Using Bone Anchors for the Treatment of Female Stress Incontinence, ASAIO Journal, 204-208 (1997).

Pereyra: A Simplified Surgical Procedure for the Correction of Stress Incontinence in Women, West J. Surg. Obstetrics and Gynecology: 223-226 (1959).

Schaeffer et al.: Endoscopic Suspension of Vesical Neck for Urinary Incontinence, Urology 23: 484-494 (1984).

* cited by examiner

METHODS AND DEVICES FOR THE TREATMENT OF URINARY INCONTINENCE

CROSS-REFERENCE TO RELATED APPLICATIONS

This application claims the priority to and the benefit of U.S. provisional patent application Ser. No. 60/209,234 filed on Jun. 5, 2000, which is incorporated herein by reference in its entirety.

TECHNICAL FIELD

This invention relates to methods and devices for the treatment of female urinary incontinence.

BACKGROUND INFORMATION

Stress urinary incontinence in women may be caused by urethral hypermobility. Hypermobility is a condition in which the pelvic floor fails to properly support an area between the bladder neck and mid-urethra, thus permitting the urethra to descend from its normal anatomic position in response to increases in intra-abdominal pressure, resulting in urinary incontinence.

Surgical procedures for stabilizing the urethra include suburethral slings and needle suspensions. In some sling procedures, a suburethral sling is placed around the posterior side of the urethra and the ends are attached to an anatomical support structure, for example, the Cooper's ligament, or the abdominal fascia. In some variations, however, a suburethral sling may be placed around the posterior side of the urethra with the ends left free, that is, the ends of the sling are not attached to an anatomical structure. In needle suspension methods, the urethra is suspended by fastening periurethral tissue to anatomical support structures using sutures. In one variation of both the suburethral sling and the needle suspension procedures, the sling or suture is attached to the pubic bone by a bone anchor or surgical staple. The introduction of such foreign objects into bone, however, presents a risk of bone marrow infection and/or pubic osteitis. Furthermore, drilling holes into the pubic bone and/or driving a bone anchor into the pubic bone is contraindicated for patients with osteoporosis. The common goal of suburethral sling and bladder neck suspension procedures is to return the poorly supported, hypermobile urethra to its normal retropubic position.

Suburethral sling procedures and needle suspension procedures involve cutting through vaginal and/or retropubic tissue using a sharp tunneling instrument such as a suspension needle or a suture carrier. Because suspension needles and suture carriers include a sharp tip, there is a danger that the needle or carrier may wound large blood vessels present in the operating regions. Sharp-tipped suspension needles and suture carriers also present a risk of puncturing or otherwise injuring the bladder and/or other abdominal organs. Furthermore, the sharp end of the suspension needle or the suture carrier may cause puncture wounds to the surgeon's fingers, thus presenting a potential risk of infection to both the patient and the surgeon.

Variations of suburethral sling and needle suspension procedures involve different approaches for accessing the surgical field. For example, some suburethral sling and needle suspension procedures involve open retropubic surgery, where the surgical field is accessed through an incision in the anterior abdominal wall followed by dissection with sharp instruments. Alternatively, the surgical field may be accessed through an incision in the anterior vaginal wall followed by dissection with sharp instruments. In some procedures, a combined abdominal and transvaginal approach is employed. Such procedures involving "blind" dissection with sharp instruments is highly invasive and may cause significant trauma to the patient.

SUMMARY OF THE INVENTION

Methods and instruments for treating female urinary incontinence that obviate the need for "blind" dissection with sharp instruments and/or the use of bone anchors, and thus, avoiding the ensuing complications, are disclosed.

A surgical instrument for treating urinary incontinence includes a handle and a curved shaft extending in a distal direction from the handle. The shaft terminates at its distal end in a blunt tip for blunt dissection of tissue. A grasping mechanism is located within a distal end portion of the shaft. The grasping mechanism can be a three-position window actuated by an actuator located on the handle, and can grasp and cut suture or sling material. The instrument is adapted to transvaginally access interior tissue within a human body, and to attach sutures or slings onto a desired attachment point. The surgical instrument can be used in conjunction with a hook-type suture deployment device. The hook-type suture deployment device is adapted to attach onto the surgical instrument and to retain a suture-carrying hook. A pair of distal flaps shields the hook from surrounding tissue during insertion of the device into the body. A pair of proximal tabs release the distal flaps so as to disengage the hook from the device, allowing the hook to engage into anchoring tissue, thereby attaching a suture onto a desired location.

It is an object of this invention to provide instruments and methods for treating female stress urinary incontinence through transvaginal access and by blunt dissection. It is another object of this invention to provide instruments and methods for deploying sutures and/or slings in a surgical procedure, with reduced risk of accidental puncturing of the surgeon's fingers or injury to the patient's bladder and/or other abdominal organs.

In one another aspect, the present invention provides surgical instruments adapted for use in procedures to treat female urinary incontinence. The instrument includes a handle and a curved shaft that extends in a distal direction from the handle. The instrument is adapted to access interior tissue within a human body, such as the pelvic cavity. In one embodiment, the handle includes a friction-based gripping surface. A blunt tip is disposed at a distal end of the shaft for blunt dissection of tissue. The shaft is curved upward to facilitate transvaginal access of the pelvic cavity. In particular, the curved shaft and blunt tip allow the instrument to be moved through the endopelvic floor via blunt dissection, and to access retropubic tissue or suture attachment points such as Cooper's ligament or rectus fascia. A grasping mechanism, for grasping and cutting sutures or slings, may be located within a distal end portion of the shaft. The grasping mechanism is adapted to release a suture or a sling from the surgical instrument at a desired retropubic location. In an alternative embodiment, a hook deployment device may be attached to the surgical instrument through the grasping mechanism.

In one embodiment, the grasping mechanism comprises a window that is adapted to be positioned in an open, an intermediate, and a closed position. An actuator located on the handle of the surgical device controls the window position. In some embodiments, the actuator includes a knob or a button located on the handle. A suture or sling may be introduced into the instrument when the window is in the open position, retained in the surgical instrument when the window is in the intermediate position, and released from the instrument when the window is placed in the closed position.

In another aspect, the present invention provides a method of treating female urinary incontinence by supporting the bladder neck with an anchorless sling. In these methods, a first end of a sling is grasped through a curved surgical instrument having a blunt tip. In one embodiment, the ends of the sling are attached to sutures, and the suture is grasped in the surgical instrument. First and second incisions are made in the anterior vaginal wall on either side of the urethra, and the surgical instrument loaded with a sling is inserted into the body through the first vaginal wall incision. Guiding the surgical instrument through the endopelvic fascia, blunt dissection of tissue is performed through the endopelvic floor without cutting or piercing tissue. Once the surgical instrument carrying the sling reaches the desired location, the cutting mechanism is actuated and the suture or the sling is cut to release the sling at the retropubic location. The process is repeated on the contralateral side of the urethra thereby treating female urinary incontinence by suburethral placement of an anchorless sling.

In one embodiment, the method of treatment comprises the steps of grasping one end of the sling or the suture by placing the window of the grasping mechanism in an open position, inserting the sling or suture into the window of the grasping mechanism, placing the window into the intermediate position, transvaginally introducing the surgical instrument into the retropubic space, deploying the sling by placing the window in the closed position, thereby cutting the sling ends or the sutures, and repeating the procedure on the opposite side of the urethra.

In an alternative embodiment, the method of treatment comprises the steps of grasping one end of the sling or the suture by placing the window of the grasping mechanism in an open position, inserting the sling or suture into the window of the grasping mechanism, placing the window into the intermediate position, transvaginally introducing the surgical instrument into the retropubic space, blunt dissecting up to the pubic symphysis, tracing the pubic symphysis, "tenting" the abdominal wall with the blunt tip of the surgical instrument, making an incision in the abdominal wall at the site of the "tented" tissue, thus creating a tunnel through the vaginal wall to the abdominal wall without performing "blind" dissection with a sharp instrument. After the tunnel has been established, a sling or suture-carrying sling may be attached to the abdominal wall and/or the rectus fascia. The procedure is then repeated on the contralateral side of the urethra, resulting in a suburethral sling or suture suspension of the urethra.

In another aspect, the present invention relates to a device for deploying a surgical implant, such as a suture-carrying surgical hook, within a human body. The deployment device comprises a body member adapted to attach or clip onto an instrument, preferably a minimally invasive surgical tool such as the surgical instrument described above. The body member includes a hemi-cylindrical-shaped connector adapted for attachment to the grasping mechanism of the surgical instrument. The hemi-cylindrical-shaped connector includes a fold line positioned along a central axis of the body member and a grasping bar. The deployment device also includes a suture hook retainer, a pair of distal flaps, and a pair of proximal tabs.

In a preferred embodiment, the distal flaps, the pair of proximal tabs pair, and the retainer are coupled to the body member along the central axis of the convex surface of the hemi-cylindrical connector. The retainer is proximal to the proximal tabs, which is proximal to the pair of distal flaps. The distal flaps releasably attaches the curved top of the hook to the deployment device and the retainer releasably attaches the proximal end of the hook to the deployment device. The proximal tabs enclose the pointed tip of the suture carrying-hook from surrounding tissue until deployment.

The proximal tabs of the pair of proximal tabs are bendable distally toward the central axis of the body. When the device is positioned at the deployment site, the surgeon applies a retrograde force to surgical instrument thereby causing the pair of proximal tabs to bend distally toward the central axis of the body member. When the pair of proximal tabs are flexed in the distal direction 1) the pointed tip of the suture-carrying hook is exposed and 2) the proximal tabs engage the distal flaps. Upon engagement of the distal flaps by the proximal tabs, the distal flaps are driven outward in a direction generally perpendicular to the central axis of the body. Thus, when the pair of proximal tabs is flexed in the distal direction, the pointed tip of the hook is exposed and the curved top of the hook is released, permitting the tip of the hook to engage surrounding tissue, and detaching the hook from the deployment device.

In another aspect, this invention provides a surgical treatment of female stress urinary incontinence that comprises anchored placement of a suburethral sling. In this method, a sling is attached to a shaft of a hook, the hook and the attached suture are placed within a hook deployment device that includes a shield for the hook. The hook deployment device is attached by a snap fit to a curved surgical instrument that includes a blunt tip. In another embodiment, the hook deployment device may be attached to the curved surgical instrument through a grasping mechanism of the surgical instrument. The instrument and the attached deployment device are transvaginally inserted into the body through a vaginal incision. The instrument is guided through endopelvic fascia via blunt dissection, without the use of sharp instruments. The suture-carrying hook is deployed in the abdominal cavity as follows. After the hook deployment site has been accessed, the surgeon positions the deployment device so that the tip of the hook faces the desired anatomical support structure. The surgeon applies a retrograde force to the surgical instrument and the hook is then released from the deployment device and anchored at a desired location within the body, for example, the Cooper's ligament or another retropubic support structure, with the suture or sling extending from the shaft of the hook. The free end of the sling is then anchored on the contralateral side of the urethra by repeating the procedure on the opposite side of the urethra.

Other aspects, features, and embodiments of the invention will become apparent from the following description including the following description of the drawings.

BRIEF DESCRIPTION OF THE DRAWINGS

In the drawings, like reference characters generally refer to the same parts throughout the different figures. The drawings are not to scale, emphasis instead being placed upon illustrating the principles of the invention. Preferred and exemplary embodiments of the present invention are discussed further in the detailed description, with reference to the drawings, which show the following.

DETAILED DESCRIPTION OF THE INVENTION

Figure 1:
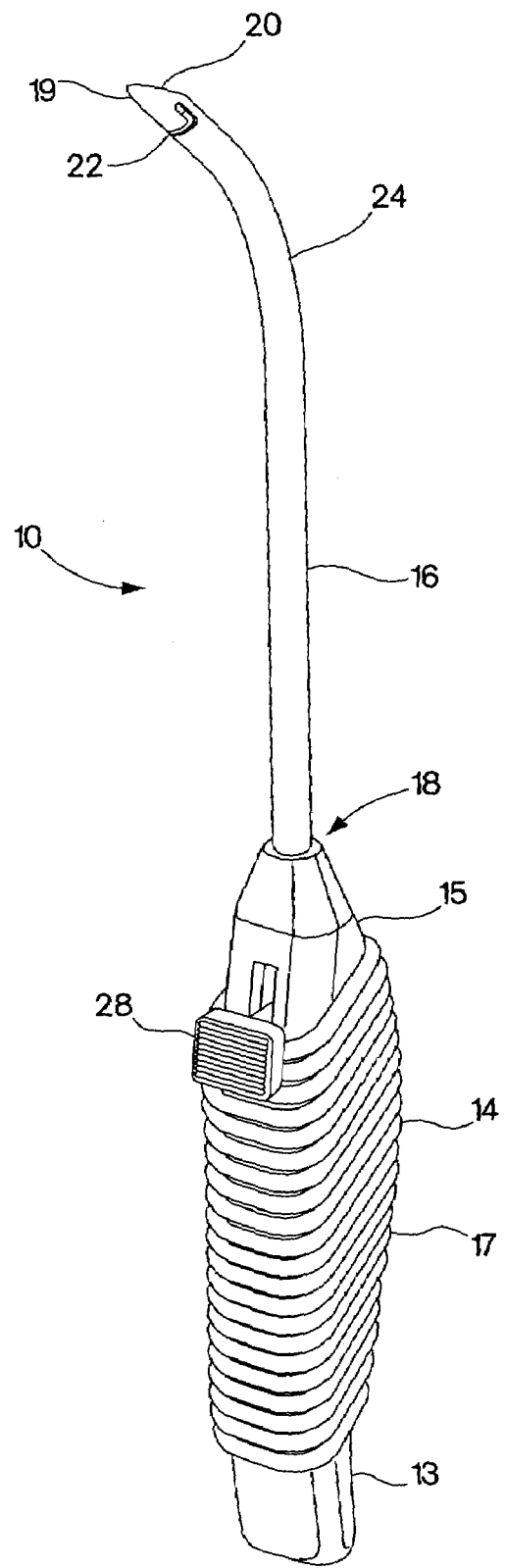
FIG. 1 shows a surgical instrument for treating female urinary incontinence constructed according to the present invention.
Figure 2:
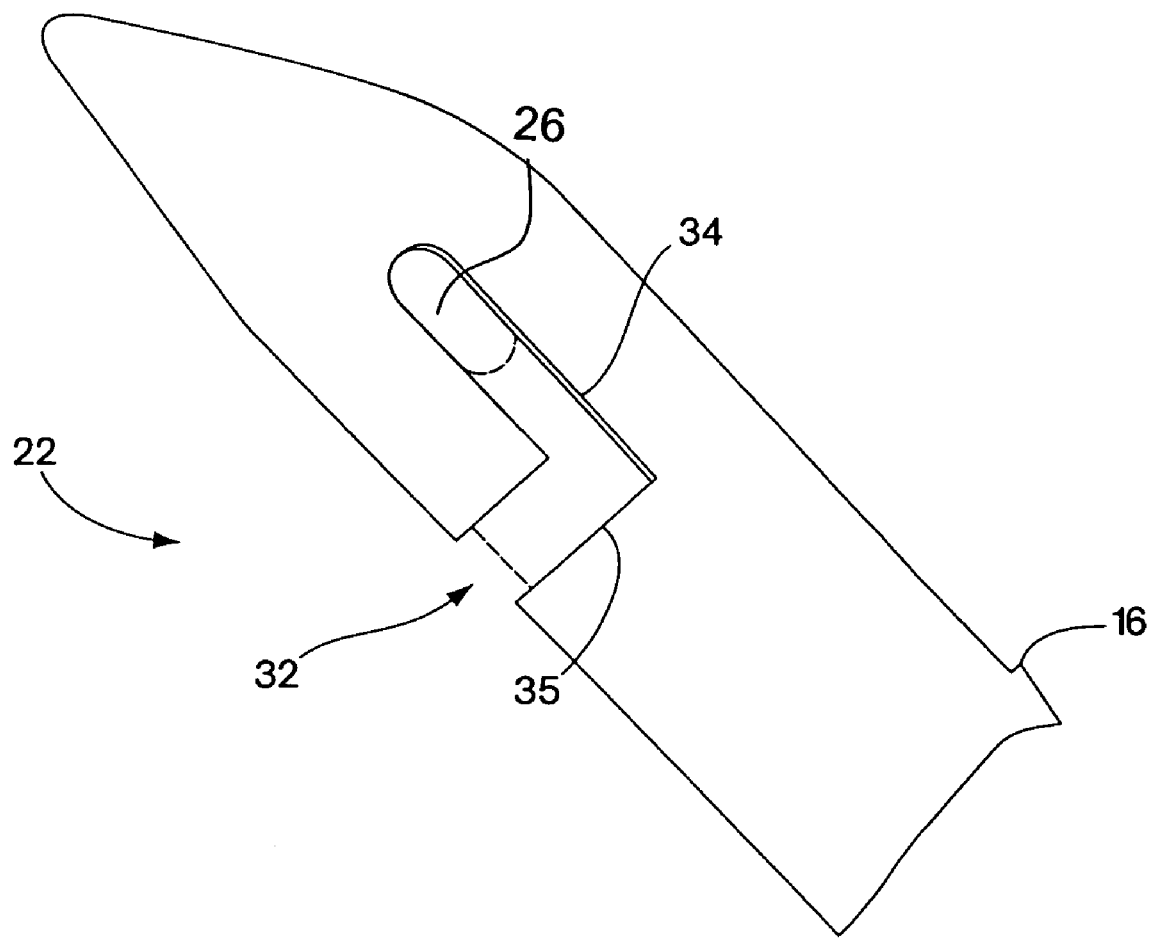
FIG. 2 shows the grasping mechanism of the surgical instrument shown in FIG. 1.

In overview, FIGS. 1 and 2 illustrate a surgical instrument 10 constructed according to the present invention for delivery of sutures or slings for the surgical treatment of female urinary incontinence. The curved surgical instrument 10 is constructed to transvaginally deliver sutures and/or slings to appropriate locations within the body to treat incontinence, without a need for dissection with sharp instruments.

The surgical instrument 10 is adaptable to be used in conjunction with a variety of tips and a variety of suture and/or sling deployment devices, providing the surgeon the flexibility to choose between different fixation methods.

Figure 3:
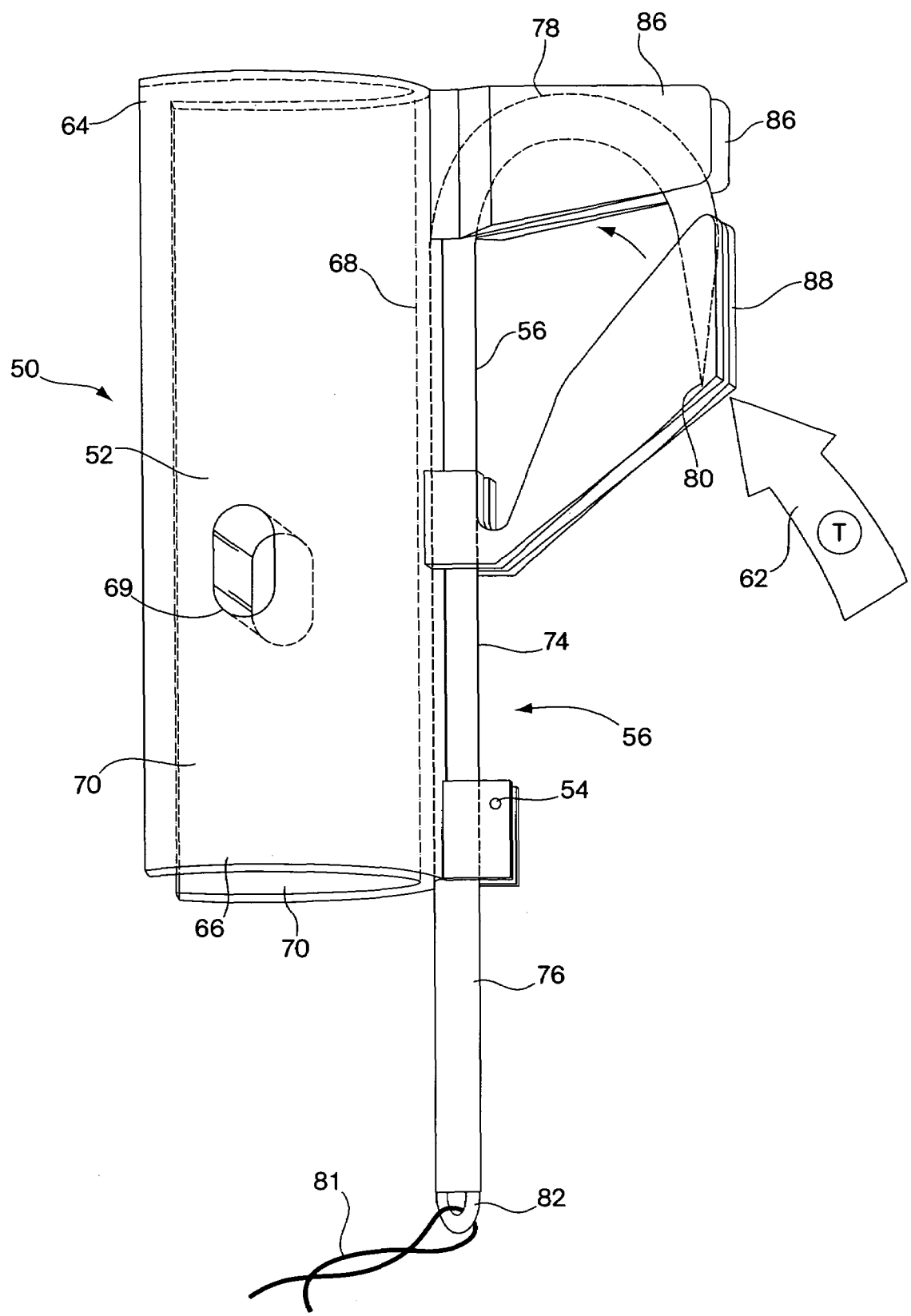
FIG. 3 shows a hook-type suture deployment device constructed according to the present invention.
Figure 4:
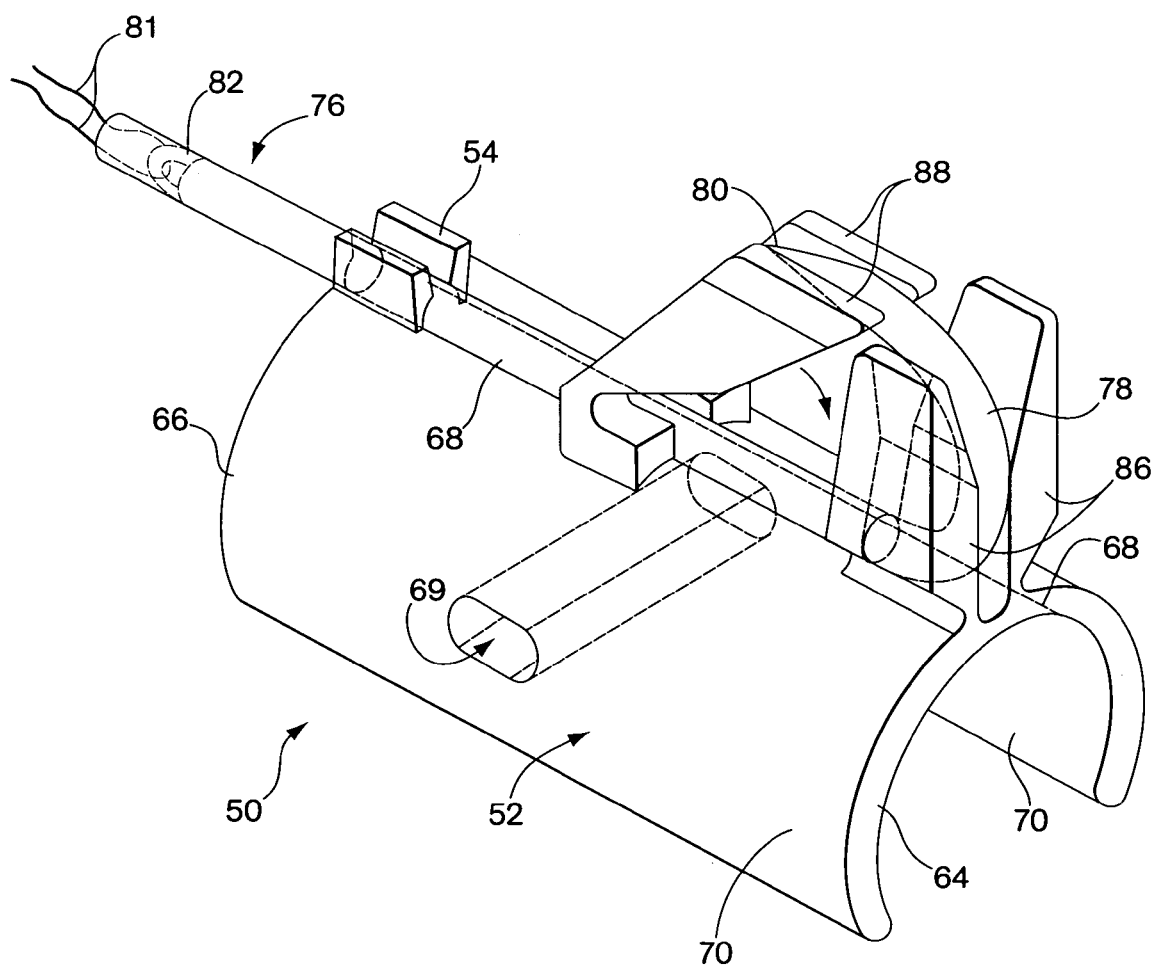
FIG. 4 shows another view of the hook-type suture deployment device constructed according to the present invention.

A hook-type suture deployment device 50 is illustrated in FIGS. 3 and 4. The hook-type suture deployment device 50 provides for suture or sling attachment onto an anatomical support structure.

Referring to FIG. 1, a curved surgical instrument 10 according to the present invention comprises a handle 14 and a shaft 16 extending in a distal direction from the handle 14. The shaft 16 has a proximal end 18 attached to the handle 14 and a distal end 19. The distal end 19 of the shaft 16 terminates in a blunt tip 20 adapted for blunt dissection of tissue. An example of the preferred shape is a "duck billed shape" wherein the shaft is cylindrical and the tip tapers at one side with a rounded surface at the distal end. A grasping mechanism 22 is located within the distal end portion of the shaft 16.

The handle 14 is adapted for gripping with ease. In preferred embodiments, the handle is at least about 4 inches in length. The handle 14 may be made of any relatively firm material, including plastics or metals. In one embodiment, the handle 14 tapers towards the proximal 13 end, to facilitate gripping by the user, as shown in FIG. 1. In another embodiment, the distal end 15 of the handle is tapered to facilitate gripping by the user. In yet another embodiment, both the distal end 15 and the proximal end 13 of the handle are tapered and thus, the central section 17 is wider than either the distal end or the proximal end of the handle 14. The handle is provided with knurling or other surface texturing to produce a high friction, non-slip gripping surface.

The elongated shaft 16 extends distally from the handle 14, and comprises a curved portion 24. The shaft 16 is curved in order to facilitate a proper transvaginal insertion and manipulation of the surgical instrument 10. The shaft 16 is generally linear at its proximal end 18 and angles upward near its distal end 19. The upward angle can be from 10 to about 135 degrees. In a preferred embodiment, the upward angle is approximately 30-60 degrees. In a most preferred embodiment, the upward angle is approximately 45 degrees. The shaft 16 may be made of any of a variety of medically acceptable materials, including steel, stainless steel, aluminum, and titanium, but is preferably made of stainless steel. The shaft 16 may have a variety of cross sectional shapes, including rectangular, hexagonal, or triangular, but preferably the shaft 16 has a circular cross section. The length of the shaft 16 is consistent with transvaginal delivery of sutures or slings. In preferred embodiments, the length of the shaft 16 is within the range of from about 6 inches to about 8 inches.

The shaft 16 terminates at its distal end 19 in a blunt tip 20. In a preferred embodiment the shaft has a circular cross section and the blunt tip 20 is beveled at the distal end with rounded edges such that the blunt tip of the shaft is "duck-billed shaped." The blunt tip 20 permits blunt dissection of tissue, rather than cutting through tissue with an instrument having sharp edges. Thus, the tissues are separated along their natural planes and damage to the traversed tissues is minimized. The blunt tip 20, together with the curved shaft 16, permit the surgeon to guide the instrument 10 from the vaginal cavity to the retropubic space so as to access the suture or sling deployment site while reducing damage to the pelvic cavity.

The grasping mechanism 22 is adapted, in a grasping mode, to grasp a suture or a sling, so that the surgical instrument 10 can deliver the suture or sling to a desired location within the body. In the cutting mode, the grasping mechanism 22 is adapted to cut the suture or sling, thereby detaching the suture or sling from the surgical instrument 10 and leaving the suture or sling at a deployment site.

In some embodiments, the grasping mechanism 22 includes a three-position window 26 operated by an actuator 28 located on the handle 14. FIG. 2 provides an enlarged view of one embodiment of the grasping mechanism 22 of the surgical instrument 10 including a three-position window 26. In this exemplary embodiment, the window 26 includes an L-shaped slot 30 that defines an opening 32 on the upper side of the shaft 16 near the distal end 19. The L-shaped slot 30 comprises a longitudinal portion 34, which is the vertical portion of the L-shaped slot. The longitudinal portion of the L-shaped slot 34 extends longitudinally along a portion of the distal end 19 of the shaft 16. The horizontal portion of the L-shaped slot 35 defines the opening 32 of the three-position window when a movable element 36 of the window is placed in the open position.

Figure 2C:
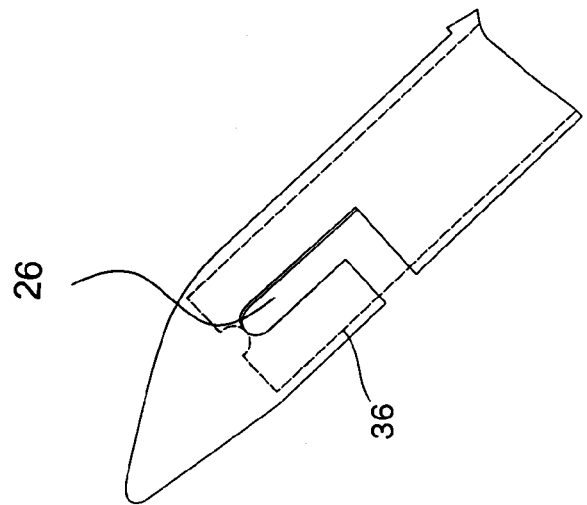
FIG. 2C shows the grasping mechanism of the surgical instrument shown in FIG. 1 with the three-position window in the closed position.
Figure 2B:
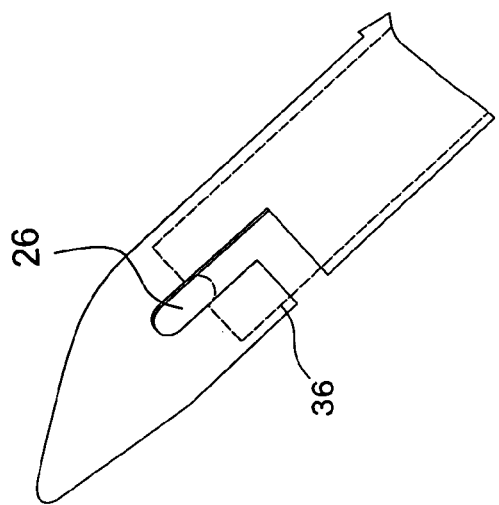
FIG. 2B shows the grasping mechanism of the surgical instrument shown in FIG. 1 with the three-position window in the intermediate position.
Figure 2A:
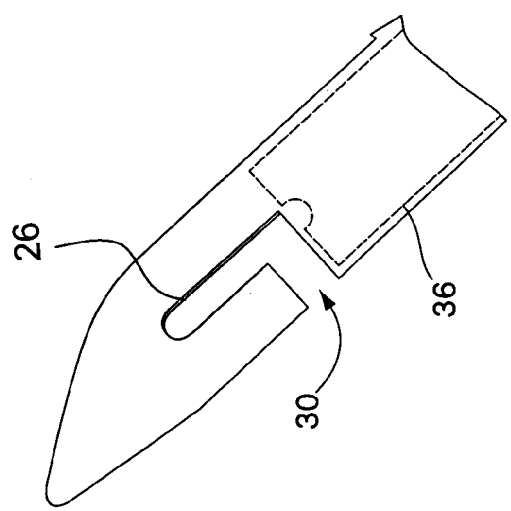
FIG. 2A shows the grasping mechanism of the surgical instrument shown in FIG. 1 with the three-position window in the open position.

In one embodiment, an actuator 28, located on the handle 14 operates the three position window 26. The actuator 28 operates a moveable element 36 positioned within the window 26. When the actuator 28 is in the open position, the moveable element 36 is retracted in the proximal location and the window 26 is open (FIG. 2A). When the actuator 28 is in the intermediate position, the moveable element 36 is extended in the distal direction, the window opening 26 is closed and there is a gap between the distal end of the slot and the distal end of the moveable element (FIG. 2B). When the actuator 28 is in the closed position, the moveable element 36 is filly extended in the distal direction, the window 26 is closed, and there is no gap between the distal end of the slot and the distal end of the moveable element (FIG. 2C). In one variation of this embodiment, the moveable element 36 includes a cutting edge (not shown) adapted to cut the suture or sling when the moveable element is placed in the closed position.

The surgical instrument 10 as illustrated in FIGS. 1 and 2 is adapted to transvaginally access an anatomical support structure that may be used as a sling and/or suture deployment site in the surgical treatment of female urinary incontinence. The curved shaft 16 and the blunt tip 20 permit transvaginal access and blunt dissection of tissue. Because the curved surgical instrument permits transvaginal access to the retropubic space, no abdominal incision is required and thus, patient morbidity is thereby reduced.

In preferred embodiments, the surgical procedure may be initiated by applying anesthesia to the female patient. The patient is placed in the lithotomy position and a pair of incisions is made in the anterior vaginal wall on either side of the urethra. The surgeon holds the curved surgical instrument 10 via the handle 14, the moveable element is set in the open position and a suture or sling material is inserted into the grasping mechanism through the opening 32 in the window 26. The actuator is set to place the moveable element 36 in the intermediate grasping position. The surgeon then inserts the instrument 10 through the anterior vaginal incision. The surgeon performs blunt dissection of tissue by using the blunt tip 20 of the instrument 10, and by digitally separating tissue and muscle. The deep endopelvic fascia is bluntly dissected in order to access the retropubic space. Blunt dissection thus proceeds from the vaginal incision through the vesicovaginal space, and into the retropubic space.

The surgeon completely traces the backside of the pubic symphysis with the instrument 10, guiding the instrument 10 through the rectus fascia, and accesses Cooper's ligament or another anatomical support structure. The surgeon, through tactile palpation, may identify the chosen anatomical support structure. Once the surgical instrument reaches the deployment site, the surgeon places the actuator in the closed position and the sling or suture is severed and thus released from the surgical device. The suture or sling material is thereby detached from the instrument 10, and attaches to the desired anatomical support structure.

The surgical instrument 10 can also be adapted to be used in conjunction with different types of suture deployment devices, which may be attached at the distal end 19 of the shaft 16. The surgical instrument 10 thus allows the surgeon to choose the type of sling or suture deployment procedure best suited to his patient's needs and to his own preferences.

FIGS. 3 and 4 show one embodiment of a hook-type suture deployment device 50 constructed according to the present invention. The hook-type suture deployment device 50 is adapted to be clipped onto a surgical tool, such as the surgical instrument 10. The suture deployment device 50 can be used to attach sutures to anatomical support surfaces such as Cooper's ligament, without the need for bone anchors. The device 50 is adapted to engage a suture-carrying hook 56 onto anchoring tissue, while shielding the sharp tip of the hook 56 during insertion and deployment of the hook.

In overview, the suture deployment device 50 comprises a body 52, a suture hook retainer 54 for retaining the suture carrying hook 56, a pair of distal flaps 86 for retaining and shielding the hook 56 from surrounding tissue during insertion of the suture deployment device 50 into the body, and a pair of proximal tabs 88 adapted to protect the tip 80 of the suture-carrying hook 56 when the device is being deployed. The proximal tabs 86 are also adapted to flex distally thus displacing the distal flaps 58 and exposing the pointed tip 80 of a suture-carrying hook 56. The hook 56 is adapted for engagement in anchoring tissue 62. The deployment device 50 may be made of any of a variety of medically acceptable materials, including plastic and/or metal, for example aluminum, titanium, or stainless steel. The dimensions of the deployment device 50 are preferably from about 2.0 cm to about 2.5 cm in length, and about 0.6 cm to about 0.9 cm in width.

The deployment device comprises a body 52 adapted to attach or clip onto an instrument, such as the curved surgical instrument 10 described above. In one embodiment, the body member includes a hemi-cylindrical-shaped connector 70 adapted for attachment to the distal section of the surgical instrument. The semi-cylindrical-shaped connector includes a central axis and aligned with a physical fold line 68. The semi-cylindrical-shaped connector may be attached to the shaft of the surgical instrument by friction fit. Optionally, the connector includes a grasping bar 69 that is adapted for engagement with the grasping mechanism of the surgical instrument. A suture hook retainer 54, a pair of distal flaps 86, and a pair of proximal tabs 88 are coupled to the body member along the central axis of the convex surface of the semi-cylindrical connector 70.

The body of the deployment device 52 comprises a retainer 54 for attaching the proximal end of the suture-carrying hook to the deployment device. The suture-carrying hook 56 includes a linear shaft 74 that has a proximal end 76 and a curved top end 78 terminating in a sharp tip 80. A suture or sling 81 is attached to the proximal end of the hook. In one embodiment, the suture or sling is threaded is an eyelet 82 formed at a proximal end 76 of the shaft 74 of the hook 56. In other embodiments, the suture or sling is integrally attached to the hook.

In an exemplary embodiment, the length of the hook 56 may be approximately 1.0-1.5 cm, and the height of the hook 56 (i.e. the perpendicular distance between the tip 80 and the linear shaft 74 may be approximately 0.2-0.5 cm. In a preferred embodiment, the height of the hook is about 0.3 cm. The hook may be made from any biologically compatible and medically acceptable material, such as titanium, aluminum, or stainless steel.

The retainer 54 is coupled to the body member 52 on the convex surface of the connector at the proximal end 66 of the body member 52. In one embodiment, the retainer comprises 54 is a snap located on the physical fold line 68 of the body 52 at the proximal end 66 of the body 52. The snap releasably holds the linear shaft 74 of the hook 56 by a friction fit.

In one embodiment, the pair of distal flaps 86 grasps and protects the curved top 78 of suture-carrying hook 56. The retainer 54 may grasp the proximal end of the suture-carrying hook 56 through, for example, friction fit. The pair of proximal tabs 88 is located adjacent to and spaced apart from the distal flaps 86 such that the pair of proximal tabs 88 contacts the distal flaps 86 when the proximal tabs 88 are flexed forward in the distal direction.

The pair of distal flaps 86 is located on the central axis of the body member 52 at the distal end 64. The pair of distal flaps 86 is adjacent to and spaced apart from the retainer 54. The shield formed by the distal flaps 86 is adapted to enclose the curved top end 78 of the hook 56. The distal flaps 86 are attached to the convex surface of the connector along the fold line 68 of the body member 52 such that one flap is positioned on each side of the fold line 68.

The proximal tabs 88 are bendable inward, toward the fold line 68 of the body 52. The proximal tabs 88 are located adjacent to and spaced apart from the distal flaps 86. The distance between the proximal tabs 88 and the distal flaps 86 is such that when the proximal tabs 88 bend inward, they engage the interior surfaces of the distal flaps 86. When the instrument is drawn in the proximal direction, the proximal tabs 88 engage the distal flaps 86. Upon engagement of the distal flaps 86 by the proximal tabs 88, the distal flaps 86 are driven outward, generally, in a direction perpendicular to the fold line 68 of the body member 52. This action exposes the hook 56. Drawing the device in the proximal direction drives the sharp tip 80 of the hook 56 into the surrounding anchoring tissue 62, and releases the hook 56 from the deployment device 50.

In operation, the surgeon attaches a suture or a sling 81 onto the proximal end 76 of a hook 56, for example through an eyelet 82 in the shaft of the hook. In alternative embodiments, the suture or sling is permanently affixed to the distal end of the hook. The shaft 74 of the hook 56 is releasably engaged by the retainer 54, and the curved top end 78 of the hook 56 is positioned within the shield formed by the distal flaps 86, which in one embodiment includes a pair of distal flaps 86 as shown in FIGS. 3 and 4. The deployment device 50 is attached a surgical tool, such as the surgical instrument 10. The surgeon inserts the surgical instrument 10 and the attached deployment device 50 transvaginally through a vaginal incision. During insertion of the device 50 into the body, the distal flaps 86 protect the hook 56 and the sharp tip 80.

The instrument 10 is guided through the pelvic cavity into the retropubic space. The suture attachment location is chosen so that sutures or sling 81, when attached to the location can support the bladder neck and thereby treat female stress urinary incontinence. The surgeon then manipulates the instrument 10 so as to work the deployment device 50 into a position from which the hook 56 can be released and engaged into a predetermined anatomical support structure, such as, the Cooper's ligament. While the device 50 is being worked into position, the proximal tabs 88 protect the hook 56. Finally, the surgeon releases the hook 56 from the deployment device 50, thereby anchoring the hook 56 into an anatomical support structure with the suture or sling 81 extending from the proximal end 76 of the hook. The hook 56 is released from the deployment device 50 by bending inward a pair of proximal tabs 88 to drive outward a pair of distal flaps 86, thereby exposing the hook 56 and allowing the hook 56 to engage onto anchoring tissue 62. The proximal tabs 88 and the distal flaps 86 reduce the risk of injury to abdominal organs by the sharp edges of an instrument. Sutures can thus be deployed and attached more safely and efficiently, with reduced patient morbidity.

The surgical instruments 10 are adapted to deliver a variety of sling materials through a transvaginal operation. As described above, slings enhance continence by providing a fixed or unfixed support for the bladder neck and/or the proximal urethra. Possible sling materials include organic materials such as rectus fascia, fascia lata, cadaveric fascia, or synthetic materials. Organic material such as rectus fascia and fascia lata tend to produce less scarring as compared to inorganic materials.

Having described certain preferred and exemplary embodiments of the invention, it will be apparent to those of ordinary skill in the art that other embodiments incorporating the concepts disclosed herein can be used without departing from the spirit and the scope of the invention. The described embodiments are to be considered in all respects only as illustrative and not limiting. Therefore, it is intended that the scope of the present invention be only limited by the following claims.

What is claimed is:

1. A surgical instrument for treating female urinary incontinence, the instrument comprising:
   a) a handle;
   b) a shaft extending in a distal direction from the handle and comprising a curved portion, the shaft being adapted to access interior tissue within a human body;
   c) a blunt tip including a solid apex disposed at a distal end of the shaft for blunt dissection of tissue; and
   d) a window including an L-shaped slot located within a distal end portion of the shaft, the L-shaped slot including a first leg extending radially inward and a second leg extending axially in a distal direction from an inner end of the first leg.

2. The surgical instrument of claim 1, wherein the shaft is adapted to transvaginally access interior tissue within a female human body.

3. The surgical instrument of claim 1, wherein the window is capable of receiving and retaining a suture or sling.

4. The surgical instrument of claim 1, wherein the handle comprises a friction based gripping surface.

5. A device for deploying an implant within a human body, the device comprising:
   a body member including
   (a) a connector adapted to attach onto an instrument;
   (b) a retainer coupled to the connector for holding the implant;
   (c) a shield located adjacent to and spaced apart from the retainer and at a distal end of the device for shielding the implant from surrounding tissue during insertion of the device into a human body; and
   (d) a pair of proximal tabs located adjacent to and spaced apart from the shield, the pair of proximal tabs being adapted to bend inward to drive the shield outward so as to expose the implant from the shield and disengage the implant from the device, thereby allowing the implant to engage into surrounding tissue.

6. The device of claim 5, wherein the implant is a surgical hook having a suture attached thereto, and the shield protects a tip of the surgical hook during insertion of the surgical hook into the human body.

7. The device of claim 5, wherein the retainer holds the implant to the body member by a friction fit.

8. The surgical instrument of claim 1 comprising an element for covering the window.

9. The surgical instrument of claim 8 comprising an actuator for operating the element, the element being movable between an open position, an intermediate position, and a closed position.

10. The surgical instrument of claim 9, wherein
    the window is adapted to receive a suture or sling when the element is placed in the open position,
    the window is adapted to retain a suture or sling when the element is placed in the intermediate position, and
    the window is adapted to release a suture or sling when the element is placed in the closed position.

11. The surgical instrument of claim 9, wherein the actuator comprises a knob located on the handle.

12. The surgical instrument of claim 9, wherein the element comprises a cutting edge.

13. The surgical instrument of claim 12, wherein the window is adapted to receive a suture or sling when the element is placed in the open position,
    the window is adapted to retain a suture or sling when the element is placed in the intermediate position, and
    the cutting edge is adapted to cut a suture or sling when the element is placed in the closed position.

14. The surgical instrument of claim 1, wherein the shaft is adapted for percutaneous access through an incision in the abdominal wall.

15. The surgical instrument of claim 1, wherein the shaft is adapted to place an implant introduced through a vaginal incision.

16. The surgical instrument of claim 1, wherein the first leg and the second leg form an angle of about 90 degrees.

17. The surgical instrument of claim 1, wherein the blunt tip is conical in shape.

* * * * *